United States Patent
Krull et al.

(10) Patent No.: US 8,067,612 B2
(45) Date of Patent: Nov. 29, 2011

(54) METHOD FOR PRODUCING BISBENZOXAZOLES

(75) Inventors: Matthias Krull, Harxheim (DE);
Alexander Lerch, Gelnhausen (DE);
Roman Morschhaeuser, Mainz (DE);
Norbert Beye, Kelkheim (DE);
Hanspeter Gethoeffer, Budenheim (DE); Helmut Ritter, Wuppertal (DE);
Sarah Schmitz, Duesseldorf (DE)

(73) Assignee: Clariant Finance (BVI) Limited, Tortola (VG)

( * ) Notice: Subject to any disclaimer, the term of this patent is extended or adjusted under 35 U.S.C. 154(b) by 16 days.

(21) Appl. No.: 12/444,630

(22) PCT Filed: Oct. 5, 2007

(86) PCT No.: PCT/EP2007/008681
§ 371 (c)(1),
(2), (4) Date: May 7, 2009

(87) PCT Pub. No.: WO2008/043496
PCT Pub. Date: Apr. 17, 2008

(65) Prior Publication Data
US 2010/0076040 A1 Mar. 25, 2010

(30) Foreign Application Priority Data
Oct. 9, 2006 (DE) .................. 10 2006 047 618

(51) Int. Cl.
*C07D 413/02* (2006.01)
(52) U.S. Cl. ........................................ 548/219
(58) Field of Classification Search .................. None
See application file for complete search history.

(56) References Cited

U.S. PATENT DOCUMENTS

| | | | |
|---|---|---|---|
| 3,024,260 A | 3/1962 | Ernst | |
| 3,113,026 A | 12/1963 | Sprung | |
| 3,395,162 A | 7/1968 | Lamberti | |
| 3,652,671 A | 3/1972 | Barron | |
| 3,682,946 A * | 8/1972 | Liechti et al. | 548/219 |
| 4,133,833 A | 1/1979 | Hull | |
| 4,582,933 A | 4/1986 | Mertens et al. | |
| 4,675,319 A | 6/1987 | Nardi et al. | |
| 4,859,796 A | 8/1989 | Hurtel et al. | |
| 4,994,541 A | 2/1991 | Dell et al. | |
| 6,017,426 A | 1/2000 | Semeria et al. | |
| 2005/0272631 A1 | 12/2005 | Miracle et al. | |
| 2005/0283011 A1 | 12/2005 | Hoong et al. | |
| 2007/0060762 A1 | 3/2007 | Kawashima et al. | |
| 2010/0010244 A1 | 1/2010 | Krull et al. | |
| 2010/0032284 A1 | 2/2010 | Krull et al. | |
| 2010/0081843 A1 | 4/2010 | Krull et al. | |
| 2010/0116642 A1 | 5/2010 | Krull et al. | |

FOREIGN PATENT DOCUMENTS

| | | |
|---|---|---|
| DE | 1139738 | 11/1962 |
| DE | 2009156 | 7/1970 |
| DE | 3209800 | 9/1983 |
| DE | 224203 | 7/1985 |
| EP | 0207901 | 1/1987 |
| EP | 0226501 | 6/1987 |
| EP | 0377177 | 7/1997 |
| EP | 0884305 | 12/1998 |
| EP | 1435364 | 7/2004 |
| WO | WO20041072031 | 8/2004 |
| WO | WO2005033062 | 4/2005 |
| WO | WO2005118526 | 12/2005 |

OTHER PUBLICATIONS

Kumar. et al., "Microwave Assisted Direct Synthesis of 2-Substituted Benzoxazoles From Carboxylic Acids Under Catalyst and Solvent-Free Conditions", SYNLETT, No. 9, 2005, pp. 1401-1404.
"Microwave Synthesis" by B. L. Hayes, CEM Publishing 2002.
Goretzki et al., Macromol. Rapid Commun. 2004, 25, 513-516.
Gelens et al., Tetrahedron Letters 2005, 46(21), 3751-3754.
M. S. Nery, et al., "Niobium pentachloride promoted conversion of carboxylic acids to carboxamides: Synthesis of the 4-aryl-112,3,4-tetrahydrolsoquinollne alkaloid structures" Synthesis, (2),272 -276, 2003.
Vazquez-Tato, M.P., "Microwave-Mediated Synthesis of Amides", SYNLETT, No. 7, 1993, p. 506.
X. Wu, et al., "Microwave Enhanced Aminocarbonylations in Water", Organic Letters, 7(15), pp. 3327-3329, 2005.
Massicot et al., Synthesis 2001 (16), 2441-2444.
Iannelli et al., Tetrahedron 2005, 61, 1509-1515.
R. Martinez-Palou, et al., "Synthesis of Long Chain 2-Alkyl-1-(2-hydroxyethyl)-2-imidazolines Under Microwave in Solvent-Free Conditions", SYNLETT 2003, No. 12, pp. 1847-1849.
R. Plantier-Royon, et al., "Synthesis of Functionalized Bis-Amides of L-(+)-Tartaric Acid and Application as Copper(II) Ligands", C.R. Chimi , 2004, pp. 119-123.
R.S. Hunter, "Conversion of Visual to Instrumental Measurements of Yellowness", 1981, JAOCS, May, pp. 606-612.
Synthewave 402 Manual, 2000, Prolabo, Support pp. (2) and Manual pp. 1-13 (total 15 pages).
Bellstein Substance Identification, BRN No. 6190607, 1981.

(Continued)

*Primary Examiner* — Kamal Saeed
(74) *Attorney, Agent, or Firm* — Tod A. Waldrop

(57) ABSTRACT

The invention relates to a method for producing bisbenzoxazoles that are interconnected by means of a system of conjugated double bonds, according to which o-aminophenols are reacted with dicarboxylic acids, the carboxyl groups of which are interconnected via a double bond or a system of conjugated double bonds, to form an ammonium salt, said ammonium salt being converted in the presence of dehydrogenating catalysts and solvents with a low dielectric loss into benzoxazol by means of microwave radiation.

16 Claims, No Drawings

OTHER PUBLICATIONS

Schmitz, et al., "Access to Poly{N-[3-(dimethylamino)propyl](meth)acrylamide} via Microwave-Assisted Synthesis and Control of LCST-Behavior in Water", Macromolecular Rapid Communications, vol. 28, No. 21, Nov. 1, 2007, pp. 2080-2083.

H.J. Bauer, et al., Makromol. Chem., 183, 1982, pp. 2971-2976.

International Search Report for PCT/EP2007/008677 Mail dated Mar. 3, 2008.

International Search Report for PCT/EP2007/008678 Mail dated Mar. 10, 2008.

International Search Report for PCT/EP2007/008679 Mail dated Feb. 4, 2008.

International Search Report for PCT/EP2007/008680 Mail dated Feb. 15, 2008.

International Search Report for PCT/EP2007/008681 Mail dated Jan. 29, 2008.

* cited by examiner

METHOD FOR PRODUCING BISBENZOXAZOLES

Bis-benzoxazol-2-yl-substituted compounds in which two benzoxazol-2-yl radicals are bonded to one another via a system of conjugated double bonds have gained industrial significance as dyes, UV absorbers and optical brighteners for natural, synthetic and semisynthetic fibers. They are used, for example, as spin brighteners, as brighteners for polyolefin fibers or for textile applications.

Benzoxazoles are prepared generally proceeding from 2-aminophenols by reaction with carboxylic acid derivatives, or by cyclization of Schiff bases or 2-hydroxyanilides.

For instance, according to DE-A-2009156, the preparation of 4,4'-bisbenzoxazole compounds from 2-aminophenols and diphenylcarboxylic acids and derivatives thereof is possible. The conversion of free dicarboxylic acids requires very long reaction times at high temperatures and leads only to low yields.

To achieve commercially satisfactory yields and qualities, the conventional preparation processes require high-reactivity carboxylic acid derivatives, for example acid anhydrides, nitriles or acid halides, for example acid chlorides, or chlorinating reagents, very specific starting materials and/or large amounts, i.e. at least stoichiometric amounts, of assistants, for example acidic catalysts, or they can be performed only under very extreme reaction conditions such as long reaction times and high reaction temperatures using specific catalysts and are thus very costly. These preparation processes form sometimes large amounts of undesired by-products such as acids and salts, which have to be removed from the product and disposed of. Increasing environmental awareness additionally requires the use of chlorinating reagents, hydrogen fluoride and metallic catalysts, owing to their corrosive properties and the air and water pollution caused by them, to be reduced or avoided entirely. However, the residues of these by-products remaining in the products can also in some cases bring about very undesired effects. For instance, halide ions and also acids lead to corrosion; residues of metal salts are often toxicologically hazardous.

Recent studies by Kumar et. al., Synlett 2005, pages 1401-1404, now describe the synthesis of benzoxazoles proceeding from 2-aminophenols and carboxylic acids with the aid of microwave radiation. Aromatic, heteroaromatic, araliphatic and also α,β-unsaturated carboxylic acids lead in good yields to 2-substituted benzoxazoles. Dicarboxylic acids, in contrast, lead, in the condensation with o-aminophenol, principally to monobenzoxazoles and, if at all, only to bisbenzoxazoles in minor amounts.

Consequently, a process has been sought for preparing bisbenzoxazoles, in which o-aminophenol and dicarboxylic acid can be reacted directly and in high, i.e. up to quantitative, yields to bisbenzoxazoles. Moreover, only minor amounts, if any, of by-products such as monobenzoxazoles and decomposition products should occur.

It has been found that bisbenzoxazoles bonded to one another via a system of conjugated double bonds can surprisingly be prepared through direct reaction of o-aminophenols with dicarboxylic acids whose carboxyl groups are bonded to one another through a system of conjugated double bonds, by irradiating with microwaves in the presence of dehydrating catalysts and solvents with low dielectric loss in high yields and with high purity.

The invention provides a process for preparing bisbenzoxazoles bonded to one another via a system of conjugated double bonds, by reacting o-aminophenols with dicarboxylic acids whose carboxyl groups are bonded to one another via a double bond or via a system of conjugated double bonds to give an ammonium salt and then converting this ammonium salt in the presence of dehydrating catalysts and solvents with low dielectric loss while irradiating with microwaves to give the benzoxazole.

Bisbenzoxazoles which are bonded to one another via a double bond or via a system of conjugated double bonds are understood to mean compounds which, between the nitrogen atoms of the terminal benzoxazole structures, possess a double bond or a through-conjugated system of π-electrons. This through-conjugated system may be formed from olefinic and/or aromatic double bonds.

Preferred bisbenzoxazoles correspond to the formula

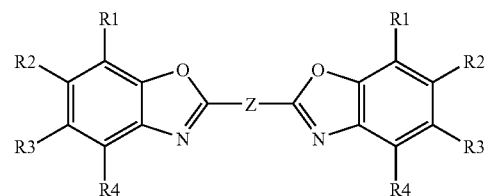

in which
$R^1$, $R^2$, $R^3$ and $R^4$ are each independently hydrogen, halogen, a hydroxyl, nitro, amino, sulfonic acid, carboxyl, carboxamide or acylamino group, or $C_1$-$C_{12}$-alkyl, $C_2$-$C_{12}$-alkenyl, $C_1$-$C_{12}$-alkoxy, phenoxy, $C_7$-$C_{12}$-alkylaryl, $C_1$-$C_{12}$-alkylsulfonyl, arylsulfonyl, $C_1$-$C_{12}$-carboxyalkyl, $C_1$-$C_{12}$-carboxamidoalkyl and sulfonic ester, where the alkyl and aryl radicals mentioned may be substituted by functional groups, and in which two adjacent radicals may form an optionally substituted, fused-on cycloaliphatic hydrocarbon ring or a mono- or polycyclic aromatic hydrocarbon ring, and
Z is —CH=CH— or a hydrocarbon radical whose ends are bonded via a system composed of conjugated double bonds.

Preferably, $R^1$, $R^2$, $R^3$ and $R^4$ are each independently hydrogen, halogen, or a hydroxyl, nitro, amino, sulfonic acid, carboxyl or carboxamide group. Preferred halogen atoms are chlorine and bromine. Preferred amino groups are primary and secondary amino groups. In a preferred embodiment, $R^1$, $R^2$, $R^3$ and $R^4$ are each independently hydrogen or $C_1$-$C_6$-alkyl radicals such as methyl or ethyl. More preferably, one or two of these radicals are $C_1$-$C_6$-alkyl radicals such as methyl or ethyl. Preferred fused-on aliphatic rings are 5- or 6-membered. Preferred fused-on mono- or polycyclic aromatic hydrocarbon rings are mono-, bi-, tri- or polycyclic, for example benzene or naphthalene systems.

The starting materials used for the inventive preparation of bisbenzoxazoles are o-aminophenols and dicarboxylic acids. These preferably correspond to the formulae

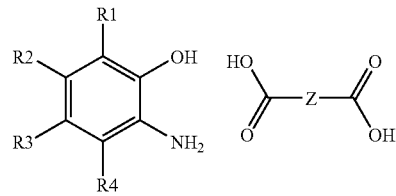

in which $R^1$, $R^2$, $R^3$, $R^4$ and Z are each as defined above.

Preferably, $R^1$, $R^2$, $R^3$ and $R^4$ are each independently hydrogen, halogen, or a hydroxyl, nitro, amino, sulfonic acid, carboxyl or carboxamide group. Preferred halogen atoms are chlorine and bromine. Preferred amino groups are primary and secondary amino groups.

In preferred o-aminophenols, $R^1$, $R^2$, $R^3$ and $R^4$ are each independently hydrogen or $C_1$-$C_6$-alkyl radicals such as methyl or ethyl. More preferably, one or two of these radicals are alkyl radicals such as methyl or ethyl. Suitable starting materials for the process according to the invention are likewise 2-aminophenols in which two adjacent $R^1$ and $R^2$, $R^2$ and $R^3$ or $R^3$ and $R^4$ radicals form an optionally substituted, fused-on cycloaliphatic, especially 5- to 6-membered, hydrocarbon ring or a mono- or polycyclic aromatic hydrocarbon ring, for example benzene or naphthalene. Suitable aminophenols are, for example, 1-amino-2-naphthol, 2-aminophenol and 2-amino-4-methylphenol. Particular preference is given to 2-aminophenol.

In a preferred embodiment, Z is a hydrocarbon radical which connects two carboxyl groups via a C=C double bond or a system composed of conjugated olefinic double bonds. The double bonds which connect the carboxyl groups are preferably trans-substituted. In a specific embodiment, Z is a substituted hydrocarbon radical which forms one or more C=C double bonds during the microwave irradiation in the process according to the invention. For example, the —$CH_2$—CH(OH)— moiety of malic acid leads to a C=C double bond with elimination of water.

In a further preferred embodiment, Z is an aromatic system having one or more than one, for example two, three, four or more, fused aromatic rings. The aromatic systems may contain heteroatoms such as N, S and/or O. The carboxyl groups are preferably bonded to the same aromatic ring, but not in the ortho position to one another. The carboxyl groups are preferably bonded in the meta positions and especially in the para positions of an aromatic ring, as, for example, in 1,4-naphthalene. In the case of polycyclic aromatic systems, the carboxyl groups may also be bonded to different rings, for example in the 1,5-positions of naphthalene.

In a further preferred embodiment, Z is a through-conjugated system composed of two or more aromatic rings which are bonded to one another via a direct C—C bond or via one or more C=C double bonds. The double bond is, or the double bonds are, preferably trans-substituted. The carboxyl groups are preferably present here in the para position to the linkage sites of the aromatic rings, as, for example, in 4,4'-bipyridine.

In a further preferred embodiment, Z is a system composed of at least one aromatic ring and at least one hydrocarbon radical comprising an olefinic double bond conjugated to it. The aromatic systems are preferably substituted in the meta position and especially in the para position to a carboxyl group by a C=C double bond or a system composed of a plurality of conjugated double bonds which bears a further carboxyl group in the terminal position. The double bond is, or the double bonds are, preferably trans-substituted.

Examples of suitable hydrocarbon Z radicals are the ethylene radical, the butadiene radical, the benzene radical, the naphthalene radical, the anthracene radical, the phenanthrene radical, the pyridine radical, the furan radical, the thiophene radical, the biphenyl radical, the styrene radical, the bisstyrene radical and the stilbene radical. Particular preference is given to the ethylene radical, the thiophene radical, the furan radical, the naphthalene radical, the stilbene radical, the biphenyl radical and the bisstyrene radical. Z thus corresponds, for example, to the following structural units:

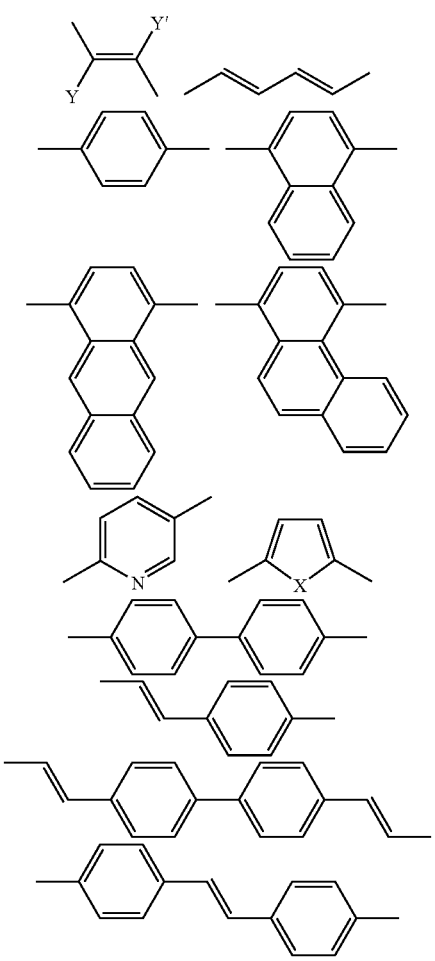

in which Y and Y' are each H or $C_1$-$C_{12}$-alkyl groups, and X is O, S or $NR^5$ where $R^5$ is hydrogen, $C_1$-$C_{30}$-alkyl, $C_6$-$C_{30}$-aryl, hydroxyl or $C_1$-$C_{20}$-hydroxyalkyl.

These radicals may bear one or more substituents, for example halogen atoms, hydroxyl, nitro, amino, sulfonic acid, sulfonic ester, carboxamide or acylamino groups, and/or $C_1$-$C_{12}$-alkyl, $C_2$-$C_{12}$-alkenyl, $C_1$-$C_{12}$-alkoxy, phenoxy, $C_7$-$C_{12}$-alkylaryl, $C_1$-$C_{12}$-alkylsulfonyl, arylsulfonyl, $C_1$-$C_{12}$-carboxyalkyl and $C_1$-$C_{12}$-carboxamidoalkyl radicals.

The dicarboxylic acids used in the process according to the invention comprise a hydrocarbon radical Z containing a through-conjugated system of π electrons between two carboxylic acid functions. Z is as defined above. Dicarboxylic acids suitable for the process according to the invention are, for example, fumaric acid, maleic acid, hexadiene-1,6-dicarboxylic acid, benzene-1,4-dicarboxylic acid, naphthalene-1,4-dicarboxylic acid, naphthalene-1,5-dicarboxylic acid, anthracene-1,4-dicarboxylic acid, thiophene-2,5-dicarboxylic acid, furan-2,5-dicarboxylic acid, stilbene-4,4'-dicarboxylic acid and biphenyl-4,4'-dicarboxylic acid. Particular preference is given to acid, benzene-1,4-dicarboxylic acid, pyridine-2,5-dicarboxylic acid, naphthalene-1,4-dicarboxylic acid, stilbene-4,4'-dicarboxylic acid and biphenyl-4,4'-dicarboxylic acid.

The dehydrating catalysts required for successful performance of the process according to the invention are generally acidic, inorganic, organometallic or organic catalysts, or mixtures of a plurality of these catalysts.

Acidic inorganic catalysts in the context of the present invention are, for example, boric acid, sulfuric acid, phosphoric acid, polyphosphoric acid, phosphonic acid, hypophosphorous acid, aluminum sulfate hydrate, alum, acidic silica gel, acidic aluminum hydroxide and zinc chloride. It has been found to be particularly useful to use boric acid, phosphoric acid, polyphosphoric acid or zinc chloride.

Additionally used and particularly preferred as acidic inorganic catalysts are aluminum compounds of the general formula $Al(OR^5)_3$ and especially titanates of the general formula $Ti(OR^5)_4$. The $R^5$ radicals may each be the same or different and are each independently selected from $C_1$-$C_{10}$-alkyl radicals, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, sec-hexyl, n-heptyl, n-octyl, 2-ethylhexyl, n-nonyl or n-decyl, $C_3$-$C_{12}$-cycloalkyl radicals, for example cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl. The $R^5$ radicals in $Al(OR^5)_3$ and $Ti(OR^5)_4$ are preferably each the same and are selected from isopropyl, butyl and 2-ethylhexyl.

Preferred acidic organometallic catalysts are, for example, selected from dialkyltin oxides $(R^5)_2SnO$ where $R^5$ is as defined above. A particularly preferred representative of acidic organometallic catalysts is di-n-butyltin oxide, which is commercially available as so-called oxo-tin or as Fascat® brands.

Preferred acidic organic catalysts are acidic organic compounds with, for example, phosphate groups, sulfonic acid groups, sulfate groups or phosphonic acid groups. Particularly preferred sulfonic acids contain at least one sulfonic acid group and at least one saturated or unsaturated, linear, branched and/or cyclic hydrocarbon radical having from 1 to 40 carbon atoms and preferably having from 3 to 24 carbon atoms. Especially preferred are aromatic sulfonic acids, especially alkylaromatic monosulfonic acids having one or more $C_1$-$C_{28}$-alkyl radicals and especially those having $C_3$-$C_{22}$-alkyl radicals. Suitable examples are methanesulfonic acid, butanesulfonic acid, benzenesulfonic acid, p-toluenesulfonic acid, xylenesulfonic acid, 2-mesitylenesulfonic acid, 4-ethylbenzenesulfonic acid, isopropylbenzenesulfonic acid, 4-butylbenzenesulfonic acid, 4-octylbenzenesulfonic acid, dodecylbenzenesulfonic acid, didodecylbenzenesulfonic acid, naphthalenesulfonic acid. It is also possible to use acidic ion exchangers as acidic organic catalysts, for example sulfonic acid group-containing poly(styrene) resins which have been crosslinked with about 2 mol % of divinylbenzene.

Particularly preferred for the performance of the process according to the invention are boric acid, phosphoric acid, polyphosphoric acid and zinc chloride. Especially preferred are boric acid and titanates of the general formula $Ti(OR^5)_4$, for example titanium tetrabutoxide and titanium tetraisopropoxide.

If it is desired to use acidic inorganic, organometallic or organic catalysts, from 0.01 to 10.0% by weight, preferably from 0.05 to 5.0% by weight, for example from 0.1 to 2.0% by weight, of catalyst is used in accordance with the invention, based on the reaction mixture.

In a further preferred embodiment, the microwave irradiation is performed in the presence of acidic solid catalysts. The solid catalyst is suspended in the ammonium salt which has optionally been admixed with solvent, or, especially in continuous processes, the ammonium salt optionally admixed with solvent is passed over a fixed bed catalyst and exposed to microwave radiation. Suitable solid catalysts are, for example, zeolites, silica gel and montmorillonite, and (partly) crosslinked polystyrenesulfonic acids, which may optionally be impregnated with catalytically active metal salts. Suitable acidic ion exchangers which are based on polystyrenesulfonic acids and can be used as solid-phase catalysts are obtainable, for example, from Rohm&Haas under the name Amberlyst®.

For successful performance of the process according to the invention, the presence of solvents is required. As a result, the reactants are suspended and at least partly dissolved, which promotes their conversion. In addition, this improves the removal of excess heat, for example by means of evaporative cooling. For this purpose, it is possible in principle to use all solvents which are inert under the reaction conditions employed and do not react with the reactants or the products formed. An important factor in the selection of suitable solvents is their polarity, which determines firstly the solution properties and secondly the degree of interaction with microwave radiation. A particularly important factor in the selection of suitable solvents is their dielectric loss $\in''$. The dielectric loss $\in''$ describes the proportion of microwave radiation which is converted to heat when a substance interacts with microwave radiation. The latter value has been found to be a particularly important criterion for the suitability of a solvent for the performance of the process according to the invention. It has been found to be particularly useful to work in solvents or solvent mixtures which exhibit minimum microwave absorption and thus make only a small contribution to the heating of the reaction system. Solvents or solvent mixtures preferred for the process according to the invention possess a dielectric loss $\in''$, measured at room temperature and 2450 MHz, of less than 10 and preferably less than 1, for example less than 0.5. An overview of the dielectric loss of different solvents can be found, for example, in "Microwave Synthesis" by B. L. Hayes, CEM Publishing 2002. Preferred solvents for the process according to the invention are solvents with $\in''$ values below 10, for example N-methylpyrrolidone, N,N-dimethylformamide, dichlorobenzene or trichlorobenzene, and especially solvents with $\in''$ values below 1. Examples of particularly preferred solvents with $\in''$ values below 1 are aromatic and/or aliphatic hydrocarbons, for example toluene, xylene, ethylbenzene, tetralin, naphthalene, ethylnaphthalene, biphenyl, diphenyl ether, hexane, cyclohexane, decane, pentadecane, decalin and mixtures thereof, and commercial hydrocarbon mixtures such as petroleum fractions, kerosene, Solvent Naphtha, ®Shellsol AB, ®Solvesso 150, ®Solvesso 200, ®Exxsol, ®Isopar and ®Shellsol types. Solvent mixtures which have $\in''$ values preferably below 10 and especially below 1 are equally preferred for the performance of the process according to the invention. In principle, the process according to the invention is also possible in solvents with $\in''$ values of 10 and higher, but this requires particular measures for complying with the maximum temperature and often leads to reduced yields. When working in the presence of solvents, the proportion thereof in the reaction mixture is preferably between 2 and 95% by weight, especially between 10 and 90% by weight and in particular between 20 and 80% by weight, for example between 30 and 70% by weight.

The process is especially suitable for preparing 1,4-bis(benzoxazol-2'-yl)benzene, 1,4-bis(benzoxazol-2'-yl)naphthalene, 4,4'-bis(benzoxazol-2'-yl)stilbene, 4,4'-bis(5-methylbenzoxazol-2'-yl)stilbene, 1,2-bis(5-methylbenzoxazol-2'-yl)ethylene and 2,5-bis(benzoxazol-2'-yl)thiophene.

In the process according to the invention, dicarboxylic acid and o-aminophenol can be reacted with one another in any desired ratios. To prepare pure compounds, suitable molar ratios between dicarboxylic acid and o-aminophenol are preferably from 10:1 to 1:20, preferably from 2:1 to 1:5, especially from 1.0:2.2 to 1.2:2.0 and especially 1.0:2.0.

In many cases, it has been found to be advantageous to work with an excess of o-aminophenol, i.e. molar ratios of o-aminophenol to dicarboxylic acid, of at least 2.01:1.00, for example between 2.1:1.0 and 10:1. This converts the dicarboxylic acid virtually quantitatively to the bisbenzoxazole. This process is particularly advantageous when the o-aminophenol used is volatile. "Volatile" means here that the amine, if appropriate under reduced pressure, can be removed by distillation from the bisbenzoxazole.

The bisbenzoxazoles are prepared by converting dicarboxylic acid and o-aminophenol to the ammonium salt and then irradiating the ammonium salt with microwaves. The ammonium salt is typically formed as an intermediate after mixing the reactants which have optionally been admixed with solvent and/or heated, in some cases also not until during the heating of the suspension of the reactants under microwave irradiation. It is preferably not isolated but rather used directly for the further conversion. The temperature rise caused by the microwave irradiation is preferably limited to a maximum of 320° C. by regulating the microwave intensity and/or cooling the reaction vessel. It has been found to be particularly useful to perform the conversion at temperatures between 100 and 300° C. and especially between 150 and 245° C., for example at temperatures between 170 and 230° C.

The duration of the microwave irradiation depends on various factors, such as the reaction volume, the geometry of the reaction chamber and the desired conversion. To achieve a conversion of more than 70% and in some cases more than 80%, for example more than 90%, the microwave irradiation is typically undertaken over a period of less than 200 minutes, preferably between 0.1 minute and 180 minutes and especially between 1 and 90 minutes, for example between 5 and 30 minutes. The intensity (power) of the microwave radiation is adjusted such that the reactants reach the desired reaction temperature within a minimum time. To subsequently maintain the temperature, the reactants can be irradiated further with reduced and/or pulsed power. To maintain the maximum temperature with simultaneously maximum microwave incidence, it has been found to be useful to cool the reactants, for example, by means of a cooling jacket, cooling tubes present in the reaction chamber through intermittent cooling between different irradiation zones, and/or by evaporative cooling by means of external heat exchangers. In a preferred embodiment, the reaction mixture is cooled directly after the microwave irradiation has ended as rapidly as possible to temperatures below 120° C., preferably below 100° C. and especially below 50° C.

Preference is given to performing the reaction at pressures between 0.1 and 200 bar and especially between 1 bar (atmospheric pressure) and 100 bar. It has been found to be particularly useful to work in closed vessels in which operation is effected above the boiling point of the reactants and/or products, of the solvent which may be present and/or above the water of reaction formed during the reaction. Typically, the pressure which is established owing to the heating of the reaction mixture is sufficient for successful performance of the process according to the invention. However, it is also possible to work under elevated pressure and/or with application of a pressure profile. In a further preferred variant of the process according to the invention, atmospheric pressure, as established, for example, in the open vessel, is employed.

To prevent side reactions and to prepare very pure products, it has been found to be useful to perform the process according to the invention in the presence of an inert protective gas, for example nitrogen, argon or helium.

The microwave irradiation is typically performed in units which possess a reaction chamber composed of a material very substantially transparent to microwaves, into which microwave radiation generated in a microwave generator is injected by suitable antenna systems. Microwave generators, for example the magnetron and the klystron, are known to those skilled in the art.

Microwaves refer to electromagnetic rays having a wavelength between about 1 cm and 1 m and frequencies between about 300 MHz and 30 GHz. This frequency range is suitable in principle for the process according to the invention. Preference is given to using, for the process according to the invention, microwave radiation with the frequencies approved for industrial, scientific and medical applications of 915 MHz, 2.45 GHz, 5.8 GHz or 27.12 GHz. It is possible to work either in monomode or quasi-monomode, or else in multimode. In the case of monomode, which places high demands on the geometry and size of apparatus and reaction chamber, a very high energy density is generated by a standing wave, especially at the maximum thereof. In multimode, in contrast, the entire reaction chamber is irradiated substantially homogeneously, which enables, for example, greater reaction volumes.

The microwave power to be injected into the reaction vessel for the performance of the process according to the invention is dependent especially on the geometry of the reaction chamber and hence on the reaction volume, and on the duration of the irradiation required. It is typically between 100 W and several hundred kW, and especially between 200 W and 100 kW, for example between 500 W and 70 kW. It can be applied at one or more sites in the reactor. It can be generated by means of one or more microwave generators.

The reaction can be carried out batchwise or preferably continuously in a flow tube, for example. It can additionally be performed in semi batchwise processes, for example continuous stirred reactors or cascade reactors. In a preferred embodiment, the reaction is performed in a closed vessel, in which case the condensate which forms and if appropriate reactants and, where present, solvents lead to a pressure build up. After the reaction has ended, the elevated pressure can be used by decompression to volatilize and remove water of reaction, and if appropriate solvents and excess reactants, and/or cool the reaction product. In a further preferred embodiment, the water of reaction formed, after cooling and/or decompression, if appropriate together with the solvent used, is removed by customary processes, for example phase separation, distillation and/or absorption. The process according to the invention can be effected equally successfully in an open vessel with evaporative cooling and/or separation of the water of reaction.

In a preferred embodiment, the process according to the invention is performed in a batchwise microwave reactor. The microwave irradiation is undertaken in a stirred vessel. To remove excess heat, cooling elements are preferably present in the reaction vessel, for example cooling fingers or cooling coils, or reflux condensors flanged onto the reaction vessel for evaporative cooling of the reaction medium. For the irradiation of relatively large reaction volumes, the microwave here is preferably operated in multimode. The batchwise embodiment of the process according to the invention allows, through variation of the microwave power, rapid or else slow heating rates, and especially the maintenance of the temperature over prolonged periods, for example several hours. The reactants and any solvents and further assistants can be initially be charged in the reaction vessel before commencement of the microwave irradiation. In a preferred embodiment of the process according to the invention, the dicarboxylic acid is suspended or brought into solution by stirring before the start of addition of the o-aminophenol in the solvent, preferably at temperatures above 50° C., for example between 100° C. and 150° C. In a further preferred embodiment, the reactants and solvents or portions thereof are not added to the reaction vessel until during the irradiation with microwaves. In a further preferred embodiment, the batchwise microwave reactor is operated with continuous supply of reactants, optionally suspended or dissolved in solvents, and simultaneous discharge of reaction mixture in the form of a semibatchwise or cascade reactor.

In a particularly preferred embodiment, the process according to the invention is performed in a continuous microwave reactor. To this end, the reaction mixture is conducted through a pressure-resistant reaction tube which is inert toward the reactants, is very substantially transparent to microwaves and is installed into a microwave oven. This reaction tube preferably has a diameter of from one millimeter to approx. 50 cm, preferably between 2 mm and 35 cm and especially between 5 mm and 15 cm, for example between 10 mm and 5 cm. Reaction tubes are understood here to mean vessels whose ratio of length to diameter is greater than 5, preferably between 10 and 100 000, more preferably between 20 and 10 000, for example between 30 and 1000. In a specific embodiment, the reaction tube is configured in the form of a jacketed tube through whose interior and exterior the reaction mixture can be conducted successively in countercurrent, in order, for example, to increase the thermal conduction and energy efficiency of the process. The length of the reaction tube is understood to mean the total distance through which the reaction mixture flows. Over its length, the reaction tube is surrounded by at least one microwave radiator, but preferably more than one, for example two, three, four, five, six, seven, eight or more microwave radiators. The microwaves are preferably injected through the tube jacket. In a further preferred embodiment, the microwaves are injected by means of at least one antenna via the tube ends proceed. The reaction tube is typically provided at the inlet with a metering pump and a manometer, and at the outlet with a pressure-retaining valve and a heat exchanger. To improve the mixing, especially in the case of heterogeneous reactions, the reaction tube may comprise mixing or conveying elements, for example conveying screws or static mixers. The o-aminophenol and dicarboxylic acid reactants, the latter preferably diluted with solvents, are preferably not mixed until shortly before entry into the reaction tube. Additionally preferably, the reactants are supplied to the process according to the invention in liquid form.

Variation of tube cross section, length of the irradiation zone (this is understood to mean the proportion of the reaction tube in which the reaction mixture is exposed to the microwave irradiation), flow rate, geometry of the microwave radiators, the microwave power injected and the temperature attained as a result are used to adjust the reaction conditions such that the maximum reaction temperature is attained as rapidly as possible and the residence time at maximum temperature remains sufficiently short that as low as possible a level of side reactions or further reactions occurs. Preference is given to operating the continuous microwave reactor in monomode or quasi-monomode. The residence time in the reaction tube is preferably between 0.1 second and 90 minutes, more preferably between one second and 60 minutes and especially between 10 seconds and 30 minutes, for example between 20 seconds and 10 minutes. To complete the reaction, if appropriate after intermediate cooling, the reaction mixture can pass through the reactor more than once. It has been found to be particularly useful when the reaction product, immediately after leaving the reaction tube, is cooled, for example by jacket cooling or decompression.

It was particularly surprising that, in spite of the only very short residence time of the ammonium salt in the microwave field in the flow tube with continuous flow, such a substantial reaction takes place without formation of significant amounts of by-product. In the case of a corresponding reaction of these ammonium salts in a flow tube with thermal jacket heating, extremely high wall temperatures are required to achieve suitable reaction temperatures, and lead to decomposition of the reactants and to the formation of colored species, but bring about virtually no bisbenzoxazole formation.

To complete the reaction, it has been found to be useful in many cases to expose the resulting crude product, after removal of water of reaction and optionally discharging product and/or by-product, again to microwave irradiation.

Typically, bisbenzoxazoles prepared by the process according to the invention are obtained as a crystal suspension and can be removed in a purity sufficient for further use by filtration and if appropriate washing with solvent. There is generally no need for a single or multiple recrystallization or reprecipitation. For specific requirements, they can, however, be purified further by customary purification processes, for example recrystallization, if appropriate in the presence of bleaches such as bleaching earth or activated carbon, reprecipitation, or via chromatographic processes.

The process according to the invention allows very rapid and inexpensive preparation of the bisbenzoxazoles bonded to one another via a system of conjugated double bonds in high yields and with high purity. Such rapid and selective reactions cannot be achieved by conventional methods, nor would be expected solely through heating to high temperatures.

The bisbenzoxazoles prepared in accordance with the invention are suitable especially as dyes, UV absorbers and optical brighteners for natural, synthetic and semisynthetic fibers, plastics and paper.

EXAMPLES

The reactions under microwave irradiation were effected in a "Discover" single-mode microwave reactor from OEM at a frequency of 2.45 GHz. The reaction vessels were cooled by means of compressed air. Owing to the pressure conditions in the reaction vessels, the temperature had to be measured via an IR sensor at the base of the cuvette. Comparative tests with a glass fiber optic immersed into the reaction mixture found that the temperature in the reaction medium, within the temperature range relevant here, is from about 50 to 80° C. above the temperature measured at the base of the cuvette with the IR sensor.

Batchwise reactions were effected either in closed, pressure-resistant glass cuvettes with a volume of 8 ml with magnetic stirring, or under atmospheric pressure in "open" glass vessels with a volume of 50 ml with a precision glass stirrer and attached water separator. Continuous reactions were effected in pressure-rated, cylindrical glass cuvettes (approx. 10×1.5 cm; reaction volume approx. 15 ml) with an inlet tube (bottom inlet) ending above the cuvette base, and product removal at the upper end of the cuvette (jacketed tube). The pressure which builds up during the reaction was limited to a maximum of 20 bar by means of a pressure-retaining valve and released into a reservoir. The solution or suspension of the ammonium salt was pumped into the cuvette through the inlet tube and the residence time in the irradiation zone was adjusted by modifying the pump output.

The reaction conversion was determined by means of HPLC, by determining the content of target product against a calibration curve recorded with reference substance. The HPLC separation was effected on an RP column (Nucleodur® 100-5 C18) with an eluent mixture of acetonitrile, isopropanol and water in a ratio of 45:45:10. The detection was effected by means of a UV detector at 254 nm. Water determinations were effected by means of Karl-Fischer titration.

Example 1

Preparation of 1,4-bis(benzoxazol-2'-yl)naphthalene 3.55 g (16.4 mmol) of naphthalene-1,4-dicarboxylic acid and 4.05 g (37.1 mmol) of o-aminophenol were suspended in 12.1 g of tetralin and heated to 180° C. with stirring under argon for 20 minutes. The ammonium salt-containing suspension thus prepared was admixed with 0.35 g of boric acid and 0.1 g of p-toluenesulfonic acid, and exposed to microwave irradiation of 300 W in a glass vessel with a precision glass stirrer and water separator for 2 hours. A temperature of approx. 230° C. measured by means of IR sensor was attained. This temperature was kept constant by evaporative cooling. Subsequently, the reaction mixture was cooled to room temperature within 10 min, in the course of which the product crystallized out in the form of yellow needles.

HPLC of the reaction mixture showed full conversion of the naphthalene-1,4-dicarboxylic acid to 1,4-bis(2''-benzoxazolyl)naphthalene. After filtration, washing of the crystals with methanol and drying, 1,4-bis(benzoxazol-2'-yl)naphthalene was obtained with more than 99.5% purity.

Example 2

Preparation of 1,4-bis(benzoxazol-2'-yl)naphthalene in the Closed System 0.71 g (3.3 mmol) of naphthalene-1,4-dicarboxylic acid and 0.81 g (7.4 mmol) of o-aminophenol were suspended in 2.4 g of N-methylpyrrolidone in a pressure-resistant glass cuvette with stirring. The ammonium salt-containing suspension thus prepared was, after adding 169 µl of titanium tetrabutoxide, exposed to microwave irradiation of 300 W in the cuvette sealed pressure-tight with stirring and external cooling for 15 min. A temperature of approx. 225° C. measured by means of IR sensor was attained, and the pressure rose to nearly 20 bar. Subsequently, the reaction mixture was cooled to room temperature within 10 minutes, in the course of which the product crystallized out in the form of yellowish needles. The conversion based on naphthalene-1,4-dicarboxylic acid was 83%. After filtration, washing of the crystals with ethanol, extraction of residual acid by stirring with alcoholic sodium hydroxide solution and drying, 1,4-bis(benzoxazol-2'-yl)naphthalene was obtained with more than 99.5% purity. A further 15-minute microwave irradiation of the mother liquor which has been dried to remove water of reaction and consists essentially of solvent and unconverted reactants afforded a further 14% conversion (based on the amount of naphthalene-1,4-dicarboxylic acid originally used).

Example 3

Preparation of 1,2-bis(5-methylbenzoxazol-2'-yl)ethylene 2.3 g of fumaric acid and 5.52 g of o-amino-p-cresol were homogenized in 12.45 g of tetralin with heating and stirring. The ammonium salt-containing suspension thus prepared was admixed with 42 mg of boric acid and 12 mg of p-toluene-sulfonic acid and, with full external cooling, exposed to microwave irradiation of 300 W in the open apparatus with stirring for 30 minutes. A temperature of approx. 220° C. measured by means of an IR sensor was attained. Subsequently, the reaction mixture was cooled to room temperature within 10 minutes. The yield of 1,2-bis(5-methylbenzoxazol-2'-yl)ethylene based on fumaric acid was 65%.

After filtering, washing the crystals with methanol, extracting residual acid by stirring with alcoholic sodium hydroxide solution and drying, 1,2-bis(5-methylbenzoxazol-2'-yl)ethylene was obtained with more than 98% purity.

Example 4

Continuous Preparation of 1,4-bis(benzoxazol-2'-yl)naphthalene 108 g (0.5 mol) of naphthalene-1,4-dicarboxylic acid and 120 g (1.1 mol) of o-aminophenol were dissolved in 500 g of N-methylpyrrolidone while heating to 130° C. The solution of the ammonium salt thus prepared was, after addition of 11 g of titanium tetrabutoxide, pumped continuously via the base inlet through the glass cuvette fixed in the microwave cavity. The delivery output of the pump was adjusted such that the residence time in the cuvette and hence in the irradiation zone was about 15 minutes. A microwave power of 200 W was employed with air cooling, and a temperature of 230° C. measured by means of an IR sensor was obtained. After leaving the glass cuvette, the reaction mixture was cooled to 100° C. by means of a short Liebig condenser, and then, in the course of further slow cooling, 1,4-bis(benzoxazol-2'-yl)naphthalene crystallized out in the form of yellow needles.

The conversion based on naphthalene-1,4-dicarboxylic acid was 65%. After filtering, washing with ethanol, extraction of residual acid by stirring with alcoholic sodium hydroxide solution and drying, 1,4-bis(benzoxazol-2'-yl)naphthalene was obtained with more than 99.5% purity. The mother liquor consisting principally of solvent, unconverted reactants and water of reaction was, after drying, conveyed through the reaction zone again, which afforded a further 29% conversion (based on the amount of naphthalene-1,4-dicarboxylic acid originally used).

Example 5

Preparation of 1,4-bis(benzoxazol-2'-yl)naphthalene by Thermal Condensation (Comparative Example)

108 g (0.5 mol) of naphthalenedicarboxylic acid and 120 g (1.1 mol) of o-aminophenol are initially charged in 396 g of tetralin, admixed with 14 g of cyclohexanone and 5 g of boric acid, and then heated on a water separator first at 160-165° C. for 3 h and then at 200-205° C. for a further 4 h, in the course of which the reaction progresses with elimination of water. Subsequently, the mixture is cooled to 80° C. and 190 g of alcohol are run in, and the mixture is stirred at 70-75° C. for a further hour. After cooling to room temperature, the precipitated 1,4-bis(benzoxazol-2'-yl)naphthalene is filtered off, washed repeatedly with a large amount of alcohol and freed of residual acid by extractive stirring with alcoholic sodium hydroxide solution. Thereafter, the mixture is filtered, and the filtercake is washed with a large amount of water and dried. 147 g of 1,4-bis(benzoxazol-2'-yl)naphthalene (corresponding to 74% theoretical yield) of a yellowish-ochre powder with a purity of 95% are obtained.

The invention claimed is:

1. A process for preparing a bisbenzoxazole bonded to one another via a system of conjugated double bonds, of the formula

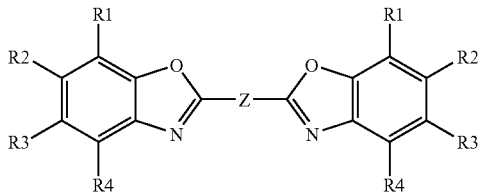

wherein
$R^1$, $R^2$, $R^3$ and $R^4$ are each independently selected from the group consisting of hydrogen, halogen, hydroxyl, nitro, amino, sulfonic acid, carboxyl, carboxamide acylamino, $C_1$-$C_{12}$-alkyl, $C_2$-$C_{12}$-alkenyl, $C_1$-$C_{12}$-alkoxy, phenoxy, $C_7$-$C_{12}$-alkylaryl, $C_1$-$C_{12}$-alkylsulfonyl, arylsulfonyl, $C_1$-$C_{12}$-carboxyalkyl, $C_1$-$C_{12}$-carboxamidoalkyl and sulfonic ester, where the alkyl and aryl radicals mentioned may be substituted by functional groups, and in which two adjacent radicals may form an optionally substituted, fused-on cycloaliphatic hydrocarbon ring or a mono- or polycyclic aromatic hydrocarbon ring, and
Z is —CH═CH— or a hydrocarbon radical whose ends are bonded via a system composed of conjugated double bonds, comprising the steps of reacting at least one o-aminophenol with at least one dicarboxylic acid whose carboxyl groups are bonded to one another via a double bond or via a system of conjugated double bonds to give an ammonium salt and subsequently converting this ammonium salt in the presence of at least one dehydrating catalyst and at least one solvent with low dielectric loss while irradiating with microwaves to give the bisbenzoxazole.

2. The process as claimed in claim 1, wherein Z is selected from the group consisting of:

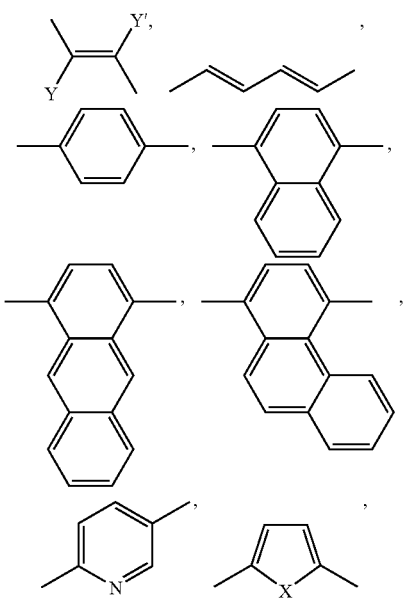

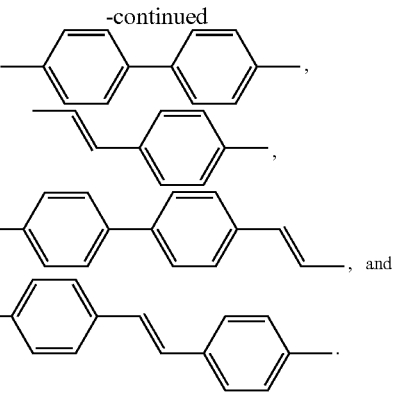

wherein Y and Y' are each H or $C_1$-$C_{12}$-alkyl groups, and X is O, S or $NR^5$
wherein $R^5$ is hydrogen, $C_1$-$C_{30}$-alkyl, $C_6$-$C_{30}$-aryl, hydroxyl or $C_1$-$C_{20}$-hydroxyalkyl.

3. The process as claimed in claim 1, wherein Z is a substituted hydrocarbon radical which forms one or more C═C double bonds during the microwave irradiation.

4. The process as claimed in claim 1, wherein the dicarboxylic acid is of the formula HOOC—Z—COOH.

5. The process as claimed in claim 1, wherein the dicarboxylic acid is selected from the group consisting of fumaric acid, maleic acid, hexadiene-1,6-dicarboxylic acid, benzene-1,4-dicarboxylic acid, naphthalene-1,4-dicarboxylic acid, naphthalene-1,5-dicarboxylic acid, anthracene-1,4-dicarboxylic acid, thiophene-2,5-dicarboxylic acid, furan-2,5-dicarboxylic acid, stilbene-4,4'-dicarboxylic acid and biphenyl-4,4'-dicarboxylic acid.

6. The process as claimed in claim 1, wherein the $R^1$, $R^2$, $R^3$ and $R^4$ radicals of the o-aminophenol are each independently hydrogen or $C_1$-$C_6$-alkyl radicals.

7. The process as claimed in claim 1, wherein two adjacent $R^1$ and $R^2$, $R^2$ and $R^3$ or $R^3$ and $R^4$ radicals of the o-aminophenol form an optionally substituted, fused-on cycloaliphatic hydrocarbon ring or a mono- or polycyclic aromatic hydrocarbon ring.

8. The process as claimed in claim 1, wherein the o-aminophenol is selected from the group consisting of 1-amino-2-naphthol, 2-aminophenol and 2-amino-4-methylphenol.

9. The process as claimed in claim 1, wherein the microwave irradiation is performed in the presence of a dehydrating catalyst.

10. The process as claimed in claim 1, wherein the solvent has a dielectric loss value of below 10.

11. The process as claimed in claim 1, wherein the reaction temperature is below 320° C.

12. The process as claimed in claim 1, wherein the reaction is performed at pressures between 0.1 and 200 bar.

13. The process as claimed in claim 1, wherein the reaction is effected continuously by irradiating with microwaves in a reaction tube through which the ammonium salt flows.

14. The process as claimed in claim 13, wherein the reaction tube consists of a nonmetallic, microwave-transparent material.

15. The process as claimed in claim 13, in which the residence time of the reaction mixture in the reaction tube is between 0.1 second and 90 minutes.

16. The process as claimed in claim 13, wherein the ratio of length to diameter of the reaction tube is at least 5.

* * * * *